United States Patent [19]

Michel

[11] Patent Number: 5,012,527

[45] Date of Patent: May 7, 1991

[54] ATHLETIC NOSE GUARD

[76] Inventor: Lorraine M. Michel, 613 S. Walter Reed Dr., Apt. 611 C, Arlington, Va. 22204

[21] Appl. No.: 11,194

[22] Filed: Feb. 5, 1987

Related U.S. Application Data

[63] Continuation-in-part of Ser. No. 891,954, Aug. 1, 1986, abandoned.

[51] Int. Cl.[5] .............................................. A61F 9/02
[52] U.S. Cl. ............................................... 2/9; 2/431
[58] Field of Search ................. 2/431, 452, 9, 439, 2/436, 206, 12, 426, 427, 432, 433, 434, 435, 437, 438, 440, 444, 448, 450

[56] References Cited

U.S. PATENT DOCUMENTS

| | | | |
|---|---|---|---|
| 387,709 | 8/1888 | Cole | 2/12 X |
| 571,437 | 11/1896 | Gray | 2/9 |
| 924,613 | 6/1909 | Hellawell | 2/9 |
| 1,336,009 | 4/1920 | Wilmer | 2/431 |
| 2,616,081 | 0/1952 | Weaver et al. | 2/9 |
| 3,049,716 | 0/1962 | Stegeman | 2/14 |
| 3,120,002 | 0/1964 | Blumenthal | 2/9 |
| 3,132,345 | 5/1964 | Keith | 2/9 |
| 3,241,155 | 0/1964 | Phillips | 2/9 |
| 3,310,812 | 0/1967 | Gaisser | 2/9 |
| 3,346,875 | 0/1965 | Weisberger | 2/9 |
| 3,672,750 | 6/1972 | Hagen | 2/430 X |
| 3,787,113 | 0/1974 | Shedrow | 351/43 |
| 3,878,563 | 4/1975 | Pulju | 2/9 |
| 3,952,331 | 4/1976 | Melville | 2/431 |
| 4,288,878 | 9/1981 | Helmbreck | 2/431 X |
| 4,494,251 | 0/1985 | Ainsworth et al. | 2/425 |
| 4,621,378 | 11/1986 | Hatchman | 2/431 X |

FOREIGN PATENT DOCUMENTS 0085746 8/1983 European Pat. Off. ............. 2/206

OTHER PUBLICATIONS

"Kings Fall as Knicks Finally Win", Sacramento Bee, Nov. 7, 1986.
"Other Protective Devices", Athletic Training and Sports Medicine, Ch. 12, p. 105, The American Academy of Orthopaedic Surgeons, 1985.
"Nasal Septal Injuries", Michael Sitler, MS, ATC, Athletic Training, Spring 1986, pp. 10–12.
"Moses Malone Unlikely for 76ers", Washington Post, Apr. 17, 1986, p. B1.

Primary Examiner—Peter A. Nerbun
Attorney, Agent, or Firm—Lane, Aitken & McCann

[57] ABSTRACT

A guard for protecting a wearer's nose includes:
  an upper edge adapted to rest on the wearer's forehead;
  a lower edge having first and second edge portions adapted to be adjacent to the wearer's cheekbones and a third edge portion adapted to be adjacent to the end of the wearer's nose, the wearer's mouth and jaw being unobstructed;
  at least one protrusion extending from the upper edge to the lower edge and covering the nose; and
  arms and straps for securing the guard to the wearer's face,
  wherein a minimum distance between the nose and a forward portion of the protrusion is greater than a distance between the first and second edge portions and the cheekbones.

13 Claims, 3 Drawing Sheets

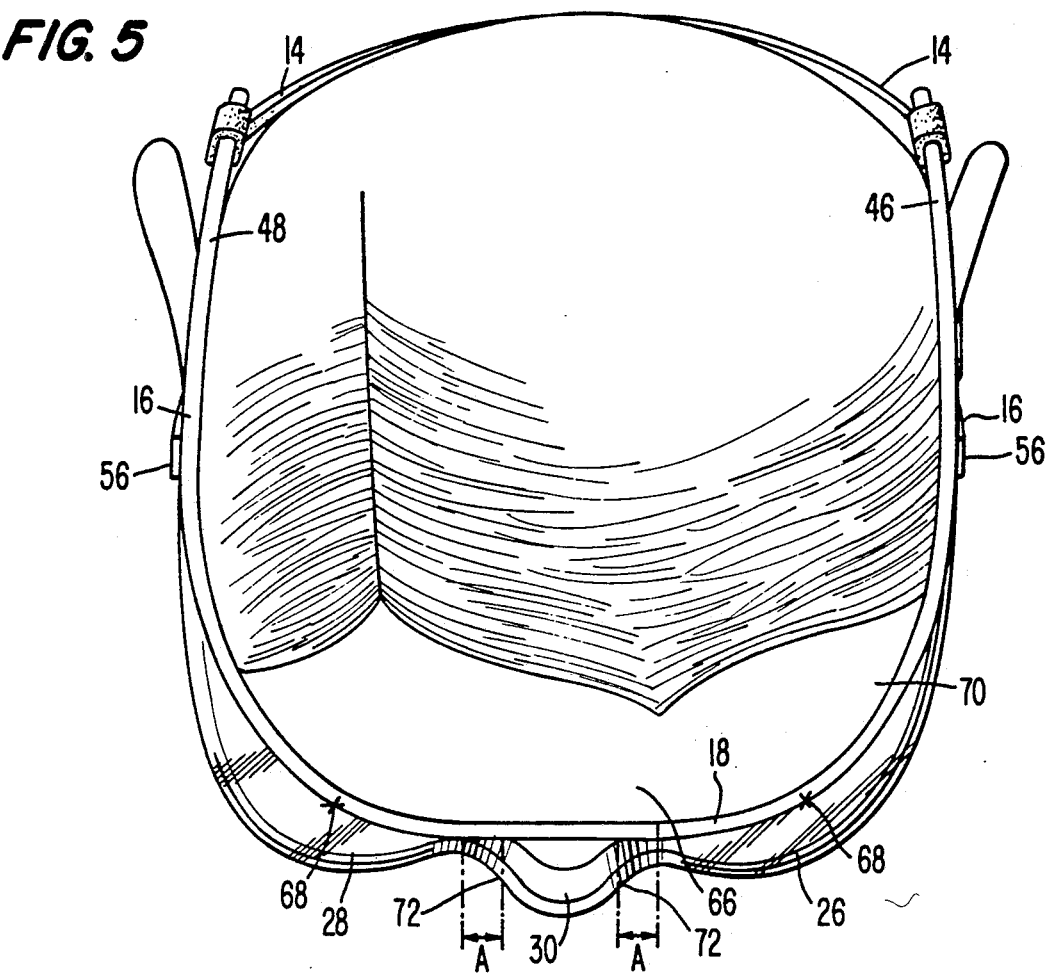
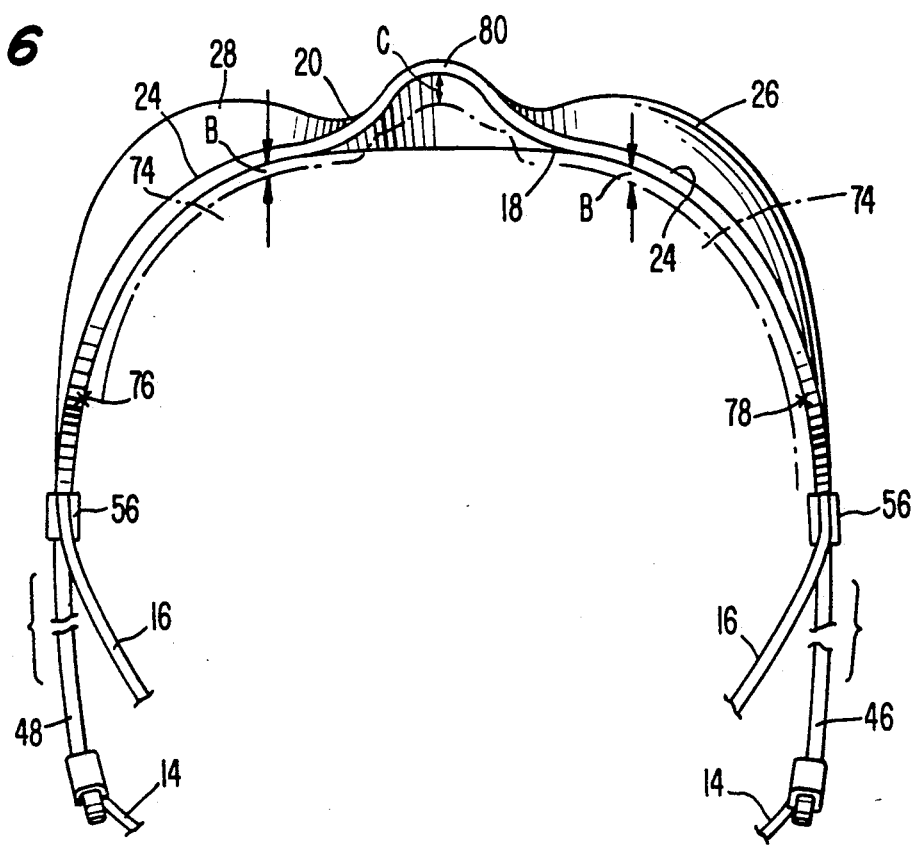

ATHLETIC NOSE GUARD

This is a continuation-in-part of U.S. application Ser. No. 891,954, filed Aug. 1, 1986, now abandoned.

BACKGROUND OF THE INVENTION

1. Field of the Invention

The present invention is directed to athletic face shields. More particularly, the present invention is related to shields for protecting the nose bridge area of the face during sports activities.

2. Discussion of the Related Art

Despite the many years over which nose guards have been allowed the opportunity to advance, it is apparent from recent experiences of prominent national basketball stars that the problem of providing a truly satisfactory guard has been a persistent one that remains unsolved. At this highly sophisticated level of athletic competition, an I-shaped nasal splint formed of a soft, deformable pad is representative of the devices used to protect a broken nose. A description of such a splint is presented at page 105 of *Athletic Training and Sports Medicine*, published by The American Academy of Orthopaedic Surgeons in 1985.

The splint is designed such that the central, vertical element of the I-shape covers the nose and an adjacent portion of the forehead, while the upper, outwardly extending arms are placed on the forehead above either eye, and the lower, outwardly extending arms are placed on the cheekbones below each eye. A strap is extended around the back of the head and is secured at either end to the ends of the upper arms, and another band extends below the ears and around the back of the neck of the wearer, and its ends are secured to the ends of the lower arms.

The splint as used in professional basketball compromises the play of the wearer and also fails to adequately protect the nose. The splint is opaque and bulky and considerably decreases the wearer's field of vision. Very little effective protection is provided the nose against blows to the face, the only real protection being afforded merely by the resiliency of the area of the pad that covers the nose. Direct and lateral blows to the region of the nose otherwise apply pressure to the nose, there being no mechanism for redistributing the impact of the blow to non-sensitive areas of the face.

It is accordingly an object of the present invention to provide an athletic nose guard that effectively protects the nose of the wearer, yet does not impede the wearer's performance.

It is a further object of the present invention to protect the nose from direct and indirect blows by distributing the impact of the blows to non-sensitive areas of the face.

It is a further object of the invention to provide an athletic nose guard that does not limit the wearer's field of vision.

It is a further object of the invention to provide an athletic nose guard that does not fog up during athletic activity.

It is a further object of the present invention to allow free movement and lack of obstruction of the wearer's mouth, so that the wearer can freely communicate with his teammates.

It is a further object of the invention to provide an athletic nose guard that is comfortable to wear.

It is a still further object of the invention to provide an athletic nose guard that is easily and effectively secured to the face.

Other objects of the present invention will become readily apparent from the foregoing detailed description.

SUMMARY OF THE INVENTION

In satisfaction of these objectives, the present invention is a guard for protecting a wearer's nose that includes an upper edge adapted to rest on the wearer's forehead and a lower edge having first and second edge portions adapted to be adjacent to the wearer's cheekbones and a third edge portion adapted to be adjacent to the end of the wearer's nose, the wearer's mouth and jaw being unobstructed. At least one protrusion extends from the upper edge to the lower edge and covers the nose, and arms and straps are provided to secure the guard to the wearer's face. A minimum distance between the nose and a forward portion of the protrusion is greater than a distance between the first and second edge portions and the cheekbones.

BRIEF DESCRIPTION OF THE DRAWINGS

FIG. 5 is a top view of the nose guard as applied to the face.

FIG. 6 is a bottom view of the nose guard as applied to the face.

DESCRIPTION OF THE PREFERRED EMBODIMENTS

Figure 1:
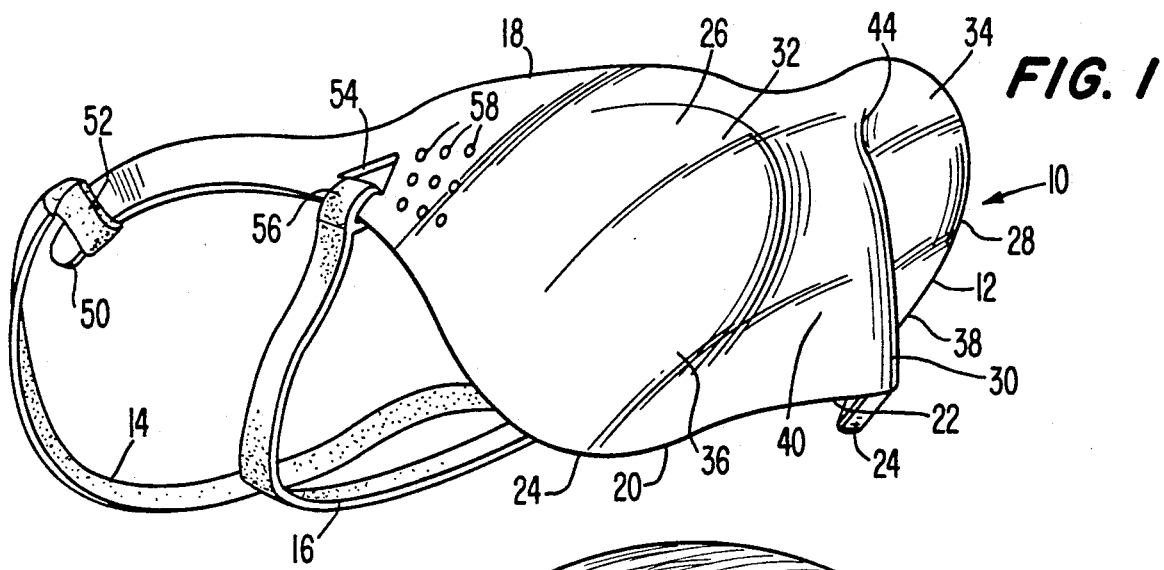
FIG. 1 is a perspective view of the athletic nose guard of the present invention.
Figure 2:
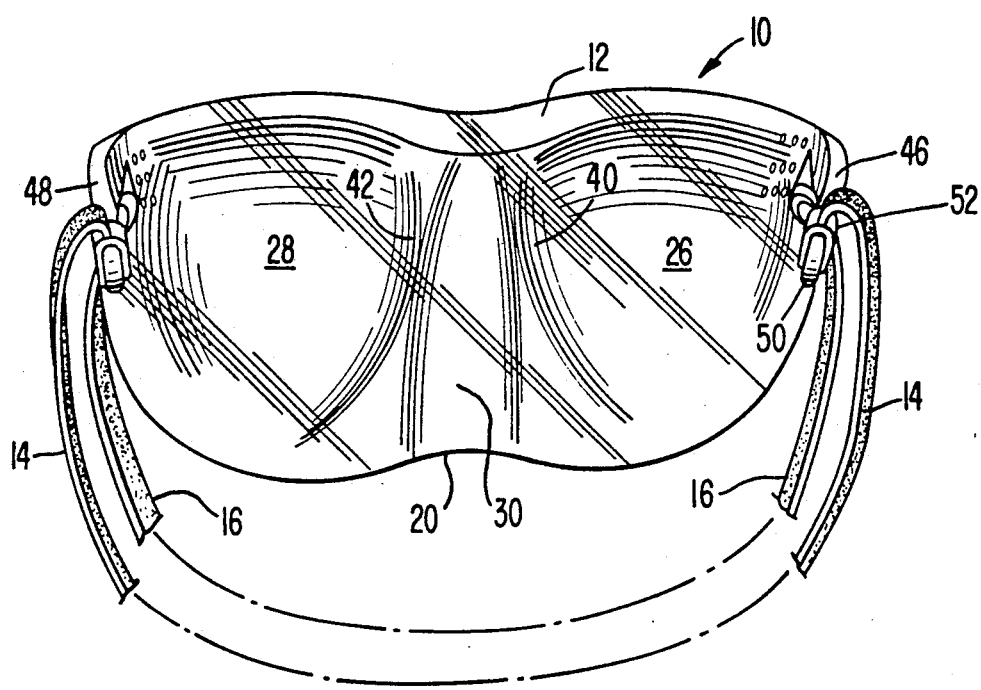
FIG. 2 is a rear view of the nose guard of FIG. 1.

A preferred embodiment of the present invention will now be described in connection with the drawings. As illustrated in FIGS. 1 and 2, nose guard 10 consists in a preferred embodiment of a rigid or semi-rigid and unbreakable plastic shield 12 and straps 14, 16. An upper edge 18 of the shield is roughly semi-circular in shape, as will be better seen in FIG. 5, such that it closely follows the shape of the wearer's forehead and temples. A bottom edge 20 is formed such that edge portion 22 adjacent to the nose extends downwardly to just cover the bottom tip of the nose, and such that edge portions 24 extend downwardly to rest upon the wearer's cheekbones. In one embodiment, relatively soft, shock-absorbent pads are applied to edges 18 and 20 where they are on or adjacent to the forehead, cheekbones and temples.

The central portion of the nose guard preferably includes three protrusions. Protrusions 26, 28, which cover each eye protrude further, relative to the plane of the wearer's face, at top portions 32, 34 of the protrusions than at lower portions 36, 38, and the areas between the upper and lower portions of protrusions 26, 28 gradually increase in degree of protrusion from bottom to top.

Standard techniques known in the art of optometry are employed to reduce to the greatest extent possible any visual aberration that may be caused by the shape of protrusions 26, 28, and to this end modifications of the shape of the protrusions are within the scope of the present invention. In an alternative embodiment, protrusions 26, 28 are eliminated, such that protrusion 30 and the remainder of the guard protect the nose, and in another embodiment, the three protrusions are combined into a single, wide protrusion. In a still further embodiment, corrective lenses replace protrusions 26, 28 to obviate the need for eyeglasses.

Protrusion 30 covers the nose and protrudes no further than protrusions 26, 28. Slight indentations 40, 42 separate the protrusions over the eyes from the protrusion over the nose, and these indentations allow the lower edge 20 to make better contact with the cheekbones. The amount by which protrusion 30 protrudes from the nose is relatively great from top 44 of the protrusion to edge portion 22. The particular extent of protrusion will be discussed in more detail in connection with FIGS. 3 through 6.

In the depicted, preferred embodiment, shield 10 tapers at either side into arms 46, 48, and a loop 52 of strap 14, which is formed of a material such as rubber that will grip the arms of the shield, is secured to end portions 50 of the arms. At the juncture of the body and arm of the shield, a triangular opening 54 is provided in the depicted embodiment, and a loop 56 of strap 16 is secured to the opening. Perforations 58 are provided just forward of opening 54 to provide optimum ventilation.

Figure 3:
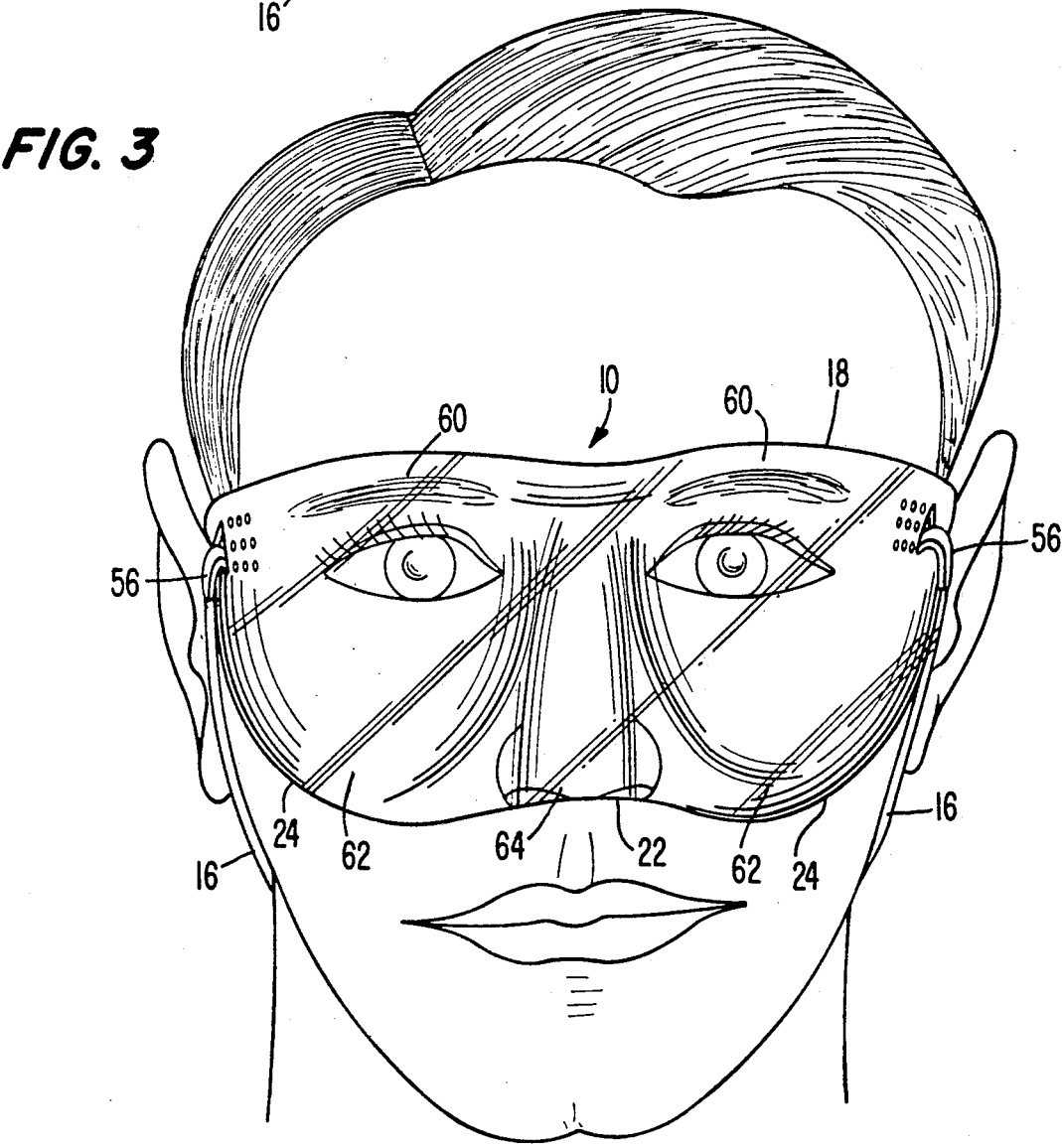
FIG. 3 is a front view of the nose guard of FIG. 1 as applied to the wearer's face.

FIG. 3 shows a front view of the nose guard as applied to the wearer's face. The guard is dimensioned such that upper edge 18 is adjacent to the wearer's forehead just above the wearer's eyebrows on eyebrow ridges 60, and such that edge portions 24 of the bottom edge are adjacent to cheekbones 62. The upper edge is partially adapted to rest on the wearer's forehead. As is best seen in this figure, edge portion 22 just covers tip 64 of the wearer's nose.

Figure 4:
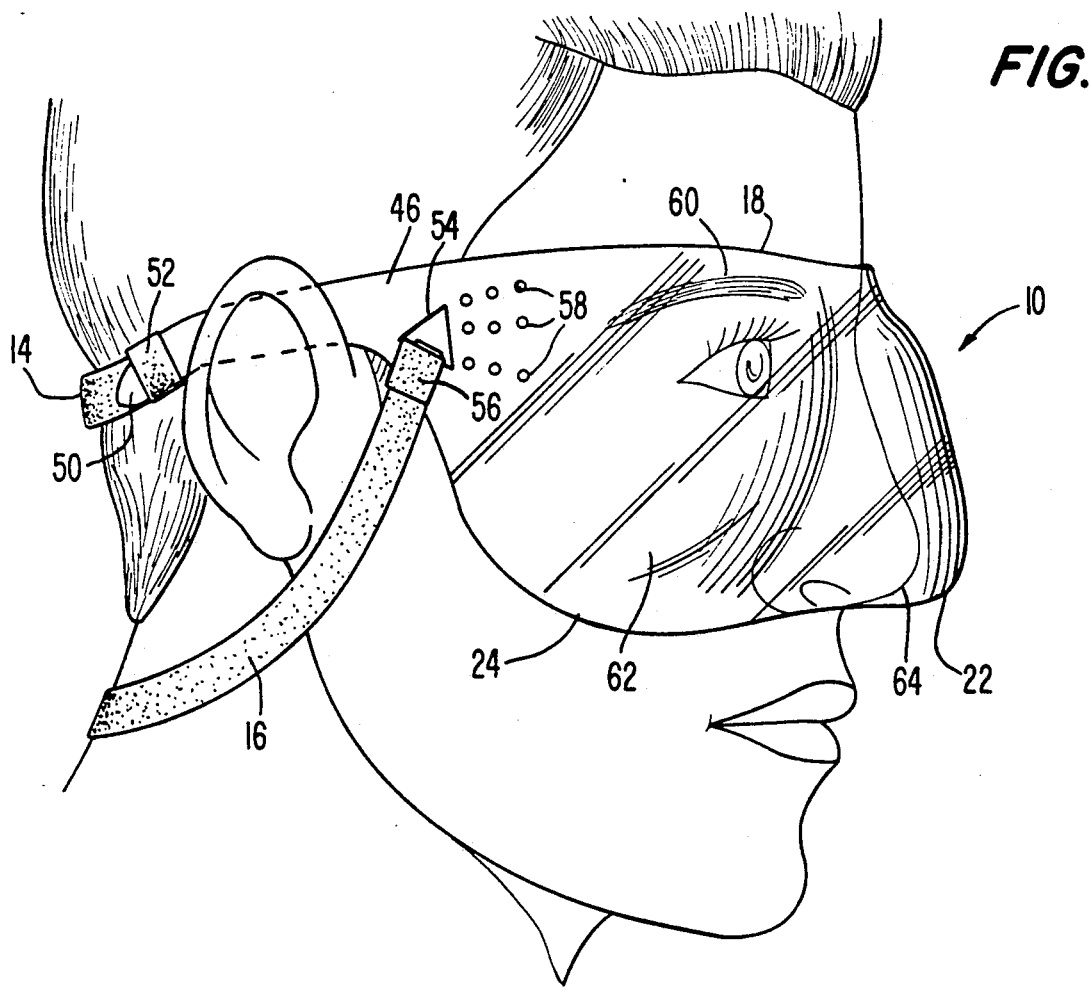
FIG. 4 is a side view of the nose guard as applied to the face.

The manner of attachment of the nose guard is best depicted in FIG. 4. Arm 46 passes over the wearer's ear, and portion 50 is positioned behind the ear. Upper strap 14 is secured to the arms and extends around the wearer's head. Lower strap 16 is positioned in front of the wearer's ear and extends downwardly and around the back of the wearer's neck. Both of the straps are preferably rendered adjustable by means well known in the art, such that the straps are readily fitted to optimize the comfort of the wearer and to ensure retention of the guard on the wearer's face.

The particular spacing of the guard from various points on the wearer's face is an important feature of the invention, as it constitutes the means by which blows to the face are directed away from the nose. The spacings are illustrated in FIGS. 5 and 6, FIG. 5 being a view of the guard as seen from the top of the wearer's head and FIG. 6 being a view of the guard as seen from below.

As seen in FIG. 5, upper edge 18, in the preferred depicted embodiment, is flush with the wearer's forehead 66 along the wearer's eyebrow ridge. The upper edge and forehead contact each other between at least two points 68 which are above the approximate centers of the wearer's eyes, and the upper edge also, in a preferred embodiment, as illustrated, contacts at least a portion of the wearer's temples 70. At the same time, sides 72 of protrusion 30 are spaced a distance from the wearer's nose, exemplified by distance A at the region of the end of the nose. The distances between the sides of the nose and the sides of the protrusion may vary along the length of the nose, but the distance between upper edge 18 and the temples of the wearer is always less than the minimum distance between the wearer's nose and the sides of protrusion 30, which is preferably about ⅛ to ¾ of an inch and is ¼ of an inch in the depicted embodiment. Preferably, any space between the temples and the upper edge is not more than about ⅛ of an inch.

The spacing of bottom edge 20 from the face is best illustrated in FIG. 6. Edge portions 24 are configured such that there is a space B between portions 24 and cheekbones 74. In a preferred embodiment, distance B is also the distance between each side of the face and lower edge 20 at points 76, 78 where the lower edge is rising towards arms 46, 48. At the same time, a distance, exemplified by distance C at the region of the end of the nose, separates the wearer's nose from front 80 of protrusion 30. The distance between the nose and the front of the protrusion may vary along the length of the nose, but the distance between portions 24 and the cheekbones is always less than the minimum distance between the wearer's nose and the front of the protrusion. Distance B is preferably about ⅛ to ¼ of an inch and is ⅛ of an inch in the depicted embodiment, and the minimum distance between the nose and the front of protrusion 30 is preferably about ¼ to ¾ of an inch and is in the depicted embodiment about ¼ of an inch. In an alternative, less preferred embodiment, distance B is reduced to 0, such that lower edge 20 rests on the cheekbone.

In the case of all of the dimensions of the guard, care is taken not to allow it to protrude unnecessarily, such that it would more likely be struck. Dimensions are selected to achieve the purposes set forth herein, without unneeded excess.

Having thus described the structure of the nose guard, the manner by which blows are directed away from the nose will be described. When struck from the front, the impact of the blow is first received along the strongest and least sensitive area of contact, which is along the eyebrow ridge. This is because the upper edge of the nose guard rests directly on the ridge, contrary to any other forward portions of the device in the preferred embodiment. The direction of the impact towards the eyebrow ridge is facilitated by the shape of protrusions 26, 28, which protrude further near the eyebrow ridge than they protrude near the cheekbones.

In the case of a very hard frontal blow, or in the case of a blow directed largely towards the bottom edge of the guard, the impact is further directed towards the cheekbones after the lower edge has been moved across distance B. At the same time, however, the nose is protected, since the distance between the nose and the front of protrusion 30 is always greater than distance B. Thus, the nose is well protected from any frontal blow.

Many blows delivered in sporting activities are not directed frontally, but instead laterally. In these cases, the present device again causes the impact to be directed towards a strong and non-sensitive portion of the face, in this case, the temples. This is because the distance between the upper edge 18 and the temples is always less than the distance between the nose and the sides of protrusion 30. When the lower edge 20 is also closely fitted to the face at points 76, 78, lateral impact is also in certain cases distributed to the sides of the face at those points.

The impact of blows delivered downwardly or upwardly is also likely to be directed away from the nose by the present invention. The impact of blows delivered downwardly is likely to be absorbed by the eyebrow ridge, and the impact of most blows delivered upwardly is likely to be absorbed by either or both the cheekbones or the eyebrow ridge.

In addition to the ability of the present invention to distribute the impact of blows to strong, non-sensitive areas of the face, the nose guard is superior for several other reasons. It is not cumbersome and is made of clear, preferably light-weight plastic, such that the wearer's field of vision is not limited. The device does not extend substantially below the wearer's nostrils, such that fogging from the wearer's breath is very unlikely. The guard similarly does not interfere with or cover the wearer's mouth or jaw, such that he can freely communicate with his teammates and, if preferred, breathe through his mouth. The straps comfortably and conveniently secure the guard firmly to the face.

It will be apparent to those skilled in the art that numerous modifications can be made to the presently described preferred embodiments without departing from the spirit and scope of the present invention.

I claim:

1. A rigid or semi-rigid guard for protecting a wearer's nose comprising:
   an upper edge partially adapted to rest on the wearer's forehead and partially adapted to be adjacent to the wearer's temples;
   a lower edge having first and second edge portions adapted to be adjacent to the wearer's cheekbones and a third edge portion adapted to be adjacent to the end of the wearer's nose, the wearer's mouth and jaw being unobstructed;
   a first protrusion extending form adjacent said upper edge to said lower edge and covering the nose and two additional protrusions that cover the wearer's eyes; and
   two arms for securing said guard to the wearer's face, one of said arms passing over one of the wearer's ears and another of said arms passing over the other of the wearer's ears; and
   securing means for holding said arms in position,
   wherein a minimum distance between the nose and a forward portion of said first protrusion is greater than a distance between said first and second edge portions and the cheekbones and, further, wherein sides of said first protrusion are spaced a minimum distance from sides of the nose, such that said minimum distance between said sides of said first protrusion and said sides of the nose is greater than a distance between said upper edge and the temples.

2. The guard of claim 1 wherein said distance between said upper edge and the temples is 0.

3. The guard of claim 1 wherein said securing means comprises a first strap secured to the arms and extending around the wearer's head, and a second strap secured to said lower edge adjacent to either arm before the ears, said second strap extending downwardly and around the back of the wearer's neck.

4. The guard of claim 1 wherein said lower edge rises from said first and second edge portions on either side of the face towards said arms and wherein points of said lower edge adjacent the sides of the face are spaced from said face a distance less than said minimum distance between said first protrusion and the sides of the nose.

5. The guard of claim 1, wherein said additional protrusions protrude further, relative to a plane of the wearer's face, at upper portions of said additional protrusions, adjacent to said upper edge, than at lower portions of said additional protrusions adjacent said lower edge.

6. The guard of claim 5, wherein areas of said additional protrusions between said upper and lower portions gradually increase in degree of protrusion from said lower to said upper portions.

7. The guard of claim 5, wherein said first protrusion protrudes no further than said additional protrusions.

8. A rigid or semi-rigid guard for protecting a wearer's nose comprising:
   an upper edge partially adapted to rest on the wearer's forehead and partially adapted to be adjacent to the wearer's temples;
   a lower edge having first and second edge portions adapted to be adjacent to the wearer's cheekbones and a third edge portion adapted to be adjacent to the wearer's nose, the wearer's mouth and jaw being unobstructed;
   a protrusion extending from said upper edge to said lower edge and covering the nose and the wearer's eyes, said protrusion protruding further adjacent to said upper edge than it protrudes adjacent to said lower edge; and
   two arms for securing said guard to the wearer's face, one of said arms passing over one of the wearer's ears and another of said arms passing over the other of the wearer's ears; and
   securing means for holding said arms in position,
   wherein a minimum distance between the nose and a forward portion of said protrusion is greater than a distance between said first and second edge portions and the cheekbones, and further wherein sides of said protrusion are spaced a minimum distance from sides of the nose, such that said minimum distance between said sides of said protrusion and said sides of the nose is greater than the distance between said upper edge and the temples.

9. A method for protecting a wearer's nose comprising the steps of:
   providing a rigid or semi-rigid guard which comprises an upper edge partially adapted to rest on the wearer's forehead and partially adapted to be adjacent to the wearer's temples, a lower edge having first and second edge portions adapted to be adjacent to the wearer's cheekbones and a third edge portion adapted to be adjacent to the end of the wearer's nose, the wearer's mouth and jaw being unobstructed, at least one protrusion extending from adjacent said upper edge to said lower edge and covering the nose, and two arms for securing said guard to the wearer's face, one of said arms passing over one of the wearer's ears and another of said arms passing over the other of the wearer's ears, said arms being held in position by securing means;
   providing said guard with a minimum distance between the nose and a forward portion of said at least one protrusion that is greater than distance between said first and second edge portions and the cheekbones;
   providing said guard with a minimum distance between sides of said at least one protrusion and sides of the nose that is greater than a distance between said upper edge and the temples; and
   positioning said guard on said wearer's head so as to protect said wearer's nose.

10. The method of claim 9, further comprising the step of providing said guard with two additional protrusions that cover the wearer's eyes, said additional protrusions protruding further, relative to a plane of the wearer's face, at upper portions of said additional protrusions adjacent said upper edge than at lower portions of said additional protrusions adjacent said lower edge.

11. The method of claim 10, further comprising the step of providing said additional protrusions with areas between said upper and lower portions that gradually increase in degree of protrusion from said lower to said upper portions.

12. The method of claim 10, further comprising the step of forming said first protrusion such that it protrudes no further from said plane than said additional protrusions.

13. The method of claim 9, wherein said lower edge rises from said first and second edge portions on either side of the face towards said arms and wherein said method further comprises the step of providing said guard with said lower edge such that points of said lower edge adjacent the sides of the face are spaced from said face a distance less than said minimum distance between said first protrusion and the sides of the nose, such that, when said guard is positioned on said wearer's head, said guard further protects said wearer's nose.

* * * * *